United States Patent [19]

Antos

[11] 4,003,826

[45] Jan. 18, 1977

[54] HYDROCARBON CONVERSION WITH AN ACIDIC MULTIMETALLIC CATALYTIC COMPOSITE

[75] Inventor: George J. Antos, Arlington Heights, Ill.

[73] Assignee: UOP Inc., Des Plaines, Ill.

[22] Filed: Oct. 28, 1975

[21] Appl. No.: 626,151

Related U.S. Application Data

[63] Continuation-in-part of Ser. No. 422,464, Dec. 6, 1973, Pat. No. 3,915,845.

[52] U.S. Cl. ............................................. 208/139
[51] Int. Cl.$^2$ ..................................... C10G 35/08
[58] Field of Search ............... 208/139; 252/466 PT

[56] References Cited

UNITED STATES PATENTS 3,852,215   12/1974   Duhaut et al. .................... 208/139
3,894,110   7/1975    Drehman ..................... 252/466 PT

*Primary Examiner*—C. Davis
*Attorney, Agent, or Firm*—James R. Hoatson, Jr.; Thomas K. McBride; William H. Page, II

[57] ABSTRACT

Hydrocarbons are converted by contacting them at hydrocarbon conversion conditions with an acidic multimetallic catalytic composite comprising a combination of catalytically effective amounts of a platinum group component, a tin or lead component, a lanthanide series component, and a halogen component with a porous carrier material. The platinum group component, tin or lead component, and halogen component are present in the multimetallic catalyst in amounts respectively, calculated on an elemental basis, corresponding to about 0.01 to about 2 wt. % platinum group metal, about 0.01 to about 5 wt. % tin or lead, and about 0.1 to about 3.5 wt. % halogen. The lanthanide series component is present in amounts corresponding to an atomic ratio of lanthanide series component to platinum group metal of about 0.1:1 to about 1.25:1. Moreover, these metallic components are uniformly dispersed throughout the porous carrier material in carefully controlled oxidation states such that substantially all of the platinum group metal is present therein in the elemental metallic state, while substantially all of the tin or lead component and of the lanthanide series component are present therein in oxidation states above that of the corresponding metal. A specific example of the type of hydrocarbon conversion process disclosed in a process for the catalytic reforming of a low-octane gasoline fraction wherein the gasoline fraction and a hydrogen stream are contacted with the novel acidic multimetallic catalyst disclosed herein at reforming conditions.

20 Claims, No Drawings

HYDROCARBON CONVERSION WITH AN ACIDIC MULTIMETALLIC CATALYTIC COMPOSITE

CROSS-REFERENCE TO RELATED APPLICATIONS

This application is a continuation-in-part of my prior copending application Ser. No. 422,464 filed Dec. 6, 1973 now U.S. Pat. No. 3,915,845, issued Oct. 28, 1975. All of the teachings of this prior application are specifically incorporated herein by reference.

DISCLOSURE

The subject of the present invention is a novel acidic multimetallic catalytic composite which has exceptional activity and resistance to deactivation when employed in a hydrocarbon conversion process that requires a catalyst having both a hydrogenation-dehydrogenation function and a selective cracking function. More precisely, the present invention involves a novel dual-function acidic multimetallic catalytic composite which, quite surprisingly, enables substantial improvements in hydrocarbon conversion processes that have traditionally used a dual-function catalyst. In another aspect, the present invention comprehends the improved processes that are produced by the use of a catalytic composite comprising a combination of catalytically effective amounts of a platinum group component, a lanthanide series component, a tin or lead component and a halogen component with a porous carrier material; specifically, an improved reforming process which utilizes the subject catalyst to improve activity, selectivity, and stability characteristics.

Composites having a hydrogenation-dehydrogenation function and a cracking function are widely used today as catalysts in many industries, such as the petroleum and petrochemical industry, to accelerate a wide spectrum of hydrocarbon conversion reactions. Generally, the cracking function is thought to be associated with an acid-acting material of the porpous, adsorptive, refractory oxide type which is typically utilized as the support or carrier for a heavy metal compound such as the transition metals or compounds of the transition metals of Groups V through VIII of the Periodic Table to which are generally attributed the hydrogenation-dehydrogenation function.

These catalytic composites are used to accelerate a wide variety of hydrocarbon conversion reactions such as hydrocracking, isomerization, dehydrogenation, hydrogenation, desulfurization, cyclization, alkylation, polymerization, cracking, hydroisomerization, etc. In many cases, the commercial applications of these catalysts are in processes where more than one of these reactions are proceeding simultaneously. An example of this type of process is reforming wherein a hydrocarbon feed stream containing paraffins and naphthenes to aromatics, dehydrocyclization of paraffins to aromatics, isomerization of paraffins and naphthenes, hydrocracking of naphthenes and paraffins and the like reactions, to produce an octane-rich or aromatic-rich product stream. Another example is a hydrocracking process wherein catalysts of this type are utilized to effect selective hydrogenation and cracking of high molecular weight unsaturated materials, selective hydrocracking of high molecular weight materials, and other like reactions, to produce a generally lower boiling, more valuable output stream. Yet another example is a hydroisomerization process wherein a hydrocarbon fraction which is relatively rich in straight-chain paraffins is contacted with a dual-function catalyst in the presence of hydrogen to produce an output stream rich in isoparaffins.

Regardless of the reaction involved or the particular process involved, it is of critical importance that the dual-function catalyst exhibit not only the capability to initially perform its specified functions, but also that it has the capability to perform them satisfactorily for prolonged periods of time. The analytical terms used in the art to measure how well a particular catalyst performs its intended functions in a particular hydrocarbon reaction environment are activity, selectivity, and stability. And for purposes of discussion here, these terms are conveniently defined for a given charge stock as follows: (1) activity is a measure of the catalyst's ability to convert hydrocarbon reactants into products at a specified severity level where severity level means the conditions used — that is, the temperature, pressure, contact time, and presence of diluents such as $H_2$; (2) selectivity refers to the amount of desired product or products obtained relative to the amount of reactants charged or converted; (3) stability refers to the rate of change with time of activity and selectivity parameters — obviously, the smaller rate implying the more stable catalyst. In a reforming process, for example, activity commonly refers to the amount of conversion that takes place for a given charge stock at a specified severity level and is typically measured by octane number of the $C_5+$ product stream; selectivity refers to the amount of $C_5+$ yield, relative to the amount of the charge, that is obtained at the particular activity or severity level; and stability is typically equated to the rate of change with time of activity, as measured by octane number of $C_5+$ product, and of selectivity, as measured by $C_5+$ yield. Actually, this last statement is not strictly correct because generally a continuous reforming process is run to produce a constant octane $C_5+$ product with severity level being continuously adjusted to attain this result; and, furthermore, the severity level is for this purpose usually varied by adjusting the conversion temperature in the reaction zone so that, in point of fact, the rate of change activity finds response in the rate of change of conversion temperature and changes in this last parameter are customarily taken as indicative of activity stability.

As is well known to those skilled in the art, the principal cause of observed deactivation of instability of a dual-function catalyst when it is used in a hydrocarbon conversion reaction is associated with the fact that coke forms on the surface of the catalyst during the course of the reaction. More specifically, in these hydrocarbon conversion processes, the conditions utilized typically result in the formation of heavy, high molecular weight, black, solid or semi-solid, carbonaceous material which coats the surface of the catalyst and reduces its activity by shielding its active sites from the reactants. In other words the performance of this dual-function catalyst is sensitive to the presence of carbonaceous deposits on the surface of the catalyst. Accordingly, the major problem facing workers in this area of the art is the development of more active and selective catalytic composites that are not as sensitive to the presence of these carbonaceous materials and/or have the capability to suppress the rate of the formation of these carbonaceous materials on the catalyst. Viewed in terms of performance parameters, the problem is to develop a dual-function catalyst having superior activity, selectivity, and stability. In particular, for a reforming process the problem is typically expressed in terms of shifting and stabalizing the $C_5+$ yield-octane relationship — $C_5+$ yield being representative of selectivity and octane being proportional to activity.

I have now found a dual-function acidic multimetallic catalytic composite which possesses improved activity, selectivity, and stability characteristics when it is employed in a process for the conversion of hydrocarbons of the type which have heretofore utilized dual-function acidic catalytic composites such as processes for isomerization, hydroisomerization, dehydrogenation, desulfurization, denitrogenization, hydrogenation, alkylation, dealkylation, hydrodealkylation, transalkylation, cyclization, dehydrocyclization, cracking, hydrocracking, reforming, disproportionation, polymerization, and the like processess. In particular, I have ascertained that an acidic catalyst, comprising a combination of catalytically effective amounts of a platinum group component, a lanthanide series component, a tin or lead component and a halogen component with a porous refractory carrier material, can enable the performance of hydrocarbon conversion processes utilizing dual-function catalysts to be substantially improved if the metallic components are uniformly dispersed throughout the carrier material in the hereinafter specified amounts and if their oxidation states are controlled to be in the states hereinafter specified. Moreover, I have determined that an acidic catalytic composite, comprising a combination of catalytically effective amounts of a platinum group component, a lanthanide series component, a tin or lead component and a chloride component with an alumina carrier material, can be utilized to substantially improve the performance of a reforming process which operates on a low-octane gasoline fraction to produce a high-ocatane reformate if the metallic components are uniformly distributed throughout the alumina carrier material in the proper amounts and if their oxidation states are fixed in the states hereinafter specified. In the case of a reforming process, the principal advantage associated with the use of the novel catalyst of the present invention involves the acquistion of the capability to operate in a stable manner in a high severity operation; for example, a low pressure reforming process designed to produce a high yield of $C_5+$ reformate having an ocatane of about 100 F-1 clear. As indicated, the present invention essentially involves the finding that the addition of a tin or lead component and a lanthanide series component to a dual-function acidic hydrocarbon conversion catalyst containing a platinum group component can enable the performance characteristics of the resulting catalyst to be sharply and materially improved, if the hereinafter specified limitations on amounts of ingredients, oxidation states of metals and distribution of metallic components in the support are met.

It is, accordingly, one object of the present invention to provide an acidic multimetallic hydrocarbon conversion catalyst having superior preformance characteristics when utilized in a hydrocarbon conversion process. A second object is to provide a multimetallic catalyst having dual-function hydrocarbon conversion performance characteristics that are relatively insensitive to the deposition of hydrocarbonaceous material thereon. A third object is to provide preferred methods of preparation of this catalytic composite which insures the achievement and maintenance of its properties. Another object is to provide an improved reforming catalyst having superior activity, selectivity and stability characteristics. Yet another object is to provide a dual-function hydrocarbon conversion catalyst which utilizes a combination of a tin or lead component and a lanthanide series component to promote an acidic catalyst containing a platinum or palladium or iridium metal component.

In brief summary, the present invention is, in one embodiment, a process for converting a hydrocarbon which comprises contacting the hydrocarbon at hydrocarbon conversion conditions with an acidic catalytic composite comprising a porous carrier material containing, on an elemental basis, about 0.01 to about 2 wt. % platinum group metal, about 0.1 to about 3.5 wt. % halogen, about 0.01 to about 5 wt. % tin or lead and a lanthanide series component in an amount sufficient to result in an atomic ratio of lanthanide series component to platinum group metal of about 0.1:1 to about 1.25:1, wherein the platinum group metal, lanthanide series component and tin or lead are uniformly dispersed throughout the porous carrier material, wherein substantially all of the platinum group metal is present in the elemental metallic state and wherein substantially all of the tin or lead and of the lanthanide series component are present in an oxidation state above that of the corresponding elemental metal.

A second embodiment involves a process for reforming a gasoline fraction which comprises contacting the gasoline fraction, under reforming conditions, with an acidic catalytic composite comprising a porous carrier material containing, on an elemental basis, about 0.5 to about 1 wt. % platinum or palladium or iridium metal, about 0.5 to about 1.5 wt. % halogen, about 0.05 to about 2 wt. % tin or lead, and a lanthanide series component in an amount sufficient to result in an atomic ratio of lanthanide series component to platinum or palladium or iriduim of about 0.4:1 to about 1:1, wherein the platinum or palladium or iridium is present in the corresponding elemental metallic state, wherein substantially all of the tin or lead is present in an oxidation state above that of the elemental metal and wherein substantially all of the lanthanide series component is present in an oxidation state above that of the corresponding elemental metal.

Other objects and embodiments of the present invention relate to additional details regarding preferred catalytic ingredients, preferred amounts of ingredients, suitable methods of composite preparation, operating conditions for use in the hydrocarbon conversion processes, and the like particulars which are hereinafter given in the following detailed discussion of each of these facets of the present invention.

The acidic multimetallic catalyst used in the process of the present invention comprises a porous carrier material or support having combined therewith catalytically effective amounts of a platinum group component, a lanthanide series component, a Group IVA metallic component, and a halogen component.

Considering first the porous carrier material utilized in the present invention, it is preferred that the material be a porous, adsorptive, high-surface area support having a surface area of about 25 to about 500 m²/g. The porous carrier material should be relatively refractory to the conditions utilized in the hydrocarbon conversion process, and it is intended to include within the scope of the present invention carrier materials which have traditionally been utilized in dual-function hydrocarbon conversion catalysts such as: (1) activated carbon, coke, or charcoal; (2) silica or silica gel, silicon carbide, clays and silicates including those synthetically-prepared and naturally-occuring, which may or may not be acid treated, for example, attapulgus clay, china clay, diatomaceous earth, fuller's earth, kaoline, kieselguhr, etc.; (3) ceramics, porcelain, crushed firebrick, bauxite; (4) refractory inorganic oxides such as alumina, titanium dioxide, zirconium dioxide, chromium oxide, zinc oxide, magnesia, thoria, boria, silica-alumina, silica-magnesia, chromia-alumina, alumina-boria, silica-zirconia, etc.; (5) crystalline zeolitic aluminosilicates such as naturally-occuring or synthetically-prepared mordenite and/or faujasite, either in the hydrogen form or in a form which has been treated with multi-valent cations; (6) spinels such as $MgAl_2O_4$, $FeAl_2O_4$, $ZnAl_2O_4$, $CaAl_2O_4$ and other like compounds have the formula $MO \cdot Al_2O_3$ where M is a metal havng a valence of 2, and (7) combinations of elements from one or more of these groups. The preferred porous carrier materials for use in the present invention are refractory inorganic oxides, with best results obtained with an alumina carrier material. Suitable alumina materials are the crystalline aluminas known as the gamma-, eta-, and theta-alumina, with gamma- or eta- alumina giving best results. In addition, in some embodiments the alumina carrier material may contain minor proportions of other well known refractory inorganic oxides such as silica, zirconia, magnesia, etc.; however, the preferred support is substantially pure gamma-, or eta-alumina. Preferred carrier materials have an apparent bulk density of about 0.3 to about 0.7 g/cc and surface area characteristics such that the average pore diameter is about 20 to 300 Angstroms, the pore volume is about 0.1 to about 1 cc/g and the surface area is about 100 to about 500 m²/g. In general, best results are typically obtained with a gamma-alumina carrier material which is used in the form of spherical particles having: a relatively small diameter (i.e. typically about 1/16 inch), an apparent bulk density of about 0.5 to about 0.6 g/cc, a pore volume of about 0.4 cc/g, and a surface area of about 175 m²/g.

The preferred alumina carrier material may be prepared in any suitable manner and may be synthetically prepared or natural occurring. Whatever type of alumina is employed it may be activated prior to use by one or more treatments including drying calcination, steaming, etc, and it may be in a form known as activated alumina, activated alumina of commerce, porous alumina, alumina gel, etc. For example, the alumina carrier may be prepared by adding a suitable alkaline reagent, such as ammonium hydroxide to a salt of aluminum such as aluminum chloride, aluminum nitrate, etc., in an amount to form an aluminum hydroxide gel which upon drying and calcining is converted to alumina. The alumina carrier may be formed in any desired shape such as spheres, pills, cakes, extrudates, powders, granules, tablets, etc., and utilized in any desired size. For the purpose of the present invention a particularly preferred form of alumina is the sphere; and alumina spheres may be continuously manufactured by the well known oil drop method which comprises: forming an alumina hydrosol by any of the techniques taught in the art and preferably by reacting aluminum metal with hydrochloric acid, combining the resulting hydrosol with a suitable gelling agent and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 300° F. to about 400° F. and subjected to a calcination procedure at a temperature of about 850° F. to about 1300° F. for a period of about 1 to about 20 hours. This treatment effects conversion of the alumina hydrogel to the corresponding crystalline gamma-alumina. See the teachings of U.S. Pat. No. 2,620,314 for additional details.

One essential constituent of the instant catalytic composite is the tin or lead component. It is an essential feature of the present invention that substantially all of the tin or lead component is present in the final catalyst in an oxidation state above that of the elemental metal. This component may be present in the catalytic composite in chemical combination with one or more of the other ingredients of the composite, or as a chemical compound of tin or lead such as the corresponding oxide, sulfide, halide, oxyhalide, oxychloride, aluminate, and the like compounds. Based on the evidence currently available, it is believed that best results are obtained when substantially all of the tin or lead component exists in the final composite as tin oxide or lead oxide, respectively, and the subsequently described oxidation and reduction steps, that are used in the preparation of the instant composite, are believed to result in an acidic multimetallic catalytic composite which contains tin oxide or lead oxide. This component can be utilized in the composite in any amount which is catalytically effective, with the preferred amount being about 0.01 to about 5 wt. % thereof and most especially about 0.05 to about 2 wt. % thereof, calculated on an elemental basis. The exact amount selected within this broad range is preferably determined as a function of the particular metal that is utilized. For instance, in the case where this component is lead, it is preferred to select the amount of this component from the low end of this range — namely about 0.01 to about 1 wt. %. Additionally, it is preferred to select the amount of lead as a function of the amount of the platinum group component as explained hereinafter. In the case where this component is tin, it is preferred to select from a relatively broader range of about 0.05 to about 2 wt. % thereof.

This tin or lead component may be incorporated in the composite in any suitable manner known to the art to result in a uniform dispersion of the metal moiety through out the carrier material such as by coprecipitation or cogellation with the porous carrier material, ion exchange with the carrier material, or impregnation of the carrier material at any stage in its preparation. It is to be noted that it is intended to include within the scope of the present invention all conventional procedures for incorporating a metallic component in a catalytic composite, and the particular method of incorporation used is not deemed to be an essential feature of the present invention so long as the tin or lead component is relatively uniformly distributed throughout the porous carrier material. One acceptable method of incorporating the tin or lead component into the catalytic composite involves cogelling the tin or lead component during the preparation of the preferred carrier material, alumina. This method typically involves the addition of a suitable soluble compound of tin or lead to the alumina hydrosol. The resulting mixture is then commingled with a suitable gelling agent, such as a relatively weak alkaline reagent, and the resulting mixture is thereafter preferably gelled by dropping into a hot oil bath as explained hereinbefore. After aging, drying and calcining the resulting particles there is obtained an intimate combination of the oxide of tin or lead and alumina. One preferred method of incorporating this component into the composite involves utilization of a soluble, decomposable compound of tin or lead to impregnate the porous carrier material either before, during or after the carrier material is calcined. In general, the solvent used during this inpregnation step is selected on the basis of its capability to dissolve the desired tin or lead compound without affecting the porous carrier material which is to be impregnated; ordinarily, good results are obtained when water is the solvent; thus the preferred tin or lead compounds for use in this impregnation step are typically water-soluble and decomposable. Examples of suitable tin or lead compounds are: stannous bromide, stannous chloride, stannic chloride, stannic chloride diamine, stannic trichloride bromide, stannic chromate, stannous fluoride, stannic iodide, stannic tartrate, lead acetate, lead bromate, lead bromide, lead chlorate, lead chloride, lead citrate, lead formate, lead lactate, lead malate, lead nitrate, lead nitrite, lead ditnionate, and the like compounds. In the case of tin, stannic or stannous chloride dissolved in water is preferred. And in the case of lead, lead nitrate in water is preferred. Regardless of which impregnation solution is utilized, the tin or lead component can be impregnated either prior to, simultaneously with, or after the other metallic components are added to the carrier material. Ordinarily, best results are obtained when this component is impregnated simultaneously with the other metallic components of the composite. Likewise, best results are ordinarily obtained when the tin or lead component is tin.

Regardless of which tin or lead compound is used in the preferred impregnation step, it is important that the metal moiety be uniformly distributed throughout the carrier material. In order to achieve this objective it is necessary to maintain the pH of the impregnation solution in a range of about 7 to about 1 or less and to dilute the impregnation solution to a volume which is approximately the same or greater than the volume of the carrier material which is impregnated. Similarly, it is preferred to use a relatively long contact time during the impregnation step ranging from about ¼ hour up to about ½ hour or more before drying to remove excess solvent in order to insure a high dispersion of the tin or lead component in the porous carrier material. The carrier material is, likewise, preferably constantly agitated during this preferred impregnation step.

A second essential ingredient of the subject catalyst is the platinum group component. That is, it is intended to cover the use of platinum or palladium or iridium or rhodium or osmium or ruthenium or mixtures thereof as a second component of the present composite. It is essential feature of the present invention that substantially all of the platinum group component exists within the final catalytic composite in the elemental metallic state (i.e. as elemental platinum or palladium or iridium etc.). Generally the amount of the second component used in the final composite is relatively small compared to the amount of the other components combined therewith. In fact, the platinum group component generally will comprise about 0.01 to about 2 wt. % of the final catalytic composite, calculated on an elemental basis. Excellent results are obtained when the catalyst contains about 0.05 to about 1 wt. % of platinum, iridium rhodium, or palladium metal. Particularly preferred mixtures of these metals are platinum and iridium and platinum and rhodium.

This platinum group component may be incorporated in the catalytic composite in any suitable manner known to result in a relatively uniform distribution of this component in the carrier material such as coprecipitation or cogellation, ion-exchange, or impregnation. The preferred method of preparing the catalyst involves the utilization of a soluble, decomposable compound of a platinum group metal to impregnate the carrier material in a relatively uniform manner. For example, this component may be added to the support by commingling the latter with an aqueous solution of chloroplatinic, chloroiridic or chloropalladic acid. Other water-soluble compounds of platinum group metals may be employed in impregnation solutions and include ammonium chloroplatinate, bromoplatinic acid, platinum dichloride, platinum tetrachloride hydrate, platinum dichlorocarbonyl dichloride, dinitrodiaminoplatinum, tetramine platinum chloride, palladium chloride, palladium nitrate, palladium sulfate, etc. The utilization of a platinum group metal chloride compound, such as chloroplatinic, chloroiridic or chloropalladic acid, is preferred since it facilitates the incorporation of both the platinum group component and at least a minor quantity of the halogen component in a single step. Hydrogen chloride or the like acid is also generally added to the impregnation solution in order to further facilitate the incorporation of the halogen component and the uniform distribution of the metallic component throughout the carrier material. In addition, it is generally preferred to impregnate the carrier material after it has been calcined in order to minimize the risk of washing away the valuable platinum or palladium compounds; however, in some cases it may be advantageous to impregnate the carrier material when it is in a gelled state.

Yet another essential of the present catalytic composite is a lanthanide series component. By the use of the generic expression "lanthanide series component" it is intended to cover the 15 elements and mixtures thereof that are commonly known as the "lanthanide series" or "rare earths". Specifically, included within this definition are the following elements: lanthanum, cerium, praseodymium, neodymium, promethium, samarium, europium, gadolinium, terbium, dysprosium, holmium, erbium, thulium, ytterbium and lutetium. This component may be present in the instant multimetallic composite in any form wherein substantially all of the lanthanide element is present in an oxidation state above that of the corresponding metal such as in chemical combination with one or more of the other ingredients of the composite, or as a chemical compound such as a lanthanide series oxide, sulfide, halide, oxychloride, aluminate, and the like. However, best results are believed to be obtained when substantially all of the lanthanide series component exists in the form of the corresponding oxide and the subsequently described oxidation and prereduction procedure is believed, on the basis of the available evidence, to result in this condition. This lanthanide series component may be utilized in the composite in any amount which is catalytically effective, with the preferred amount being about 0.01 to about 1 wt. % thereof, calculated on an elemental lanthanide basis. Typically best results are obtained with about 0.05 to about 0.5 wt. % lanthanide element. According to the present invention, it is essential to select the specific amount of lanthanide series element from within this broad weight range as a function of the amount of the platinum group component, on an atomic basis, as is explained hereinafter. The lanthanie series elements that are especially preferred for purposes of the present invention are lanthanum, cerium, and neodymium, with neodymium giving best results.

The lanthanide series component may be incorporated into the catalytic composite in any suitable manner known to those skilled in the catalyst formulation art which ultimately results in a uniform dispersion of the lanthanide series moiety in the carrier material. In addition, it may be added at any stage of the preparation of the composite — either during preparation of the carrier material or thereafter — and the precise method of incorporation used is not deemed to be critical. However, best results are obtained when the lanthanide series component is incorporated in a manner such that it is relatively uniformly distributed throughout the carrier material in a positive oxidation state or a state which is easily converted to a positive oxidation state in the subsequently described oxidation step. One preferred procedure for incorporating this component into the composite involves cogelling or coprecipitating the lanthanide series component during the preparation of the preferred carrier material, alumina. This procedure usually comprehends the addition of a soluble, decomposable compound of a lanthanide series element such as neodymium nitrate to the alumina hydrosol before it is gelled. The resulting mixture is then finished by conventional gelling, aging, drying and calcination steps as explained hereinbefore. Another preferred way of incorporating this component is an impregnation step wherein the porous carrier material is impregnated with a suitable lanthanide series compound-containing solution either before, during or after the carrier material is calcined. Preferred impregnation solutions are aqueous solutions of water-soluble, decomposable lanthanide series compounds such as a lanthanide acetate, a lanthanide bromide, a lanthanide perchlorate, a lanthanide chloride, a lanthanide iodide, a lanthanide nitrate, and the like compounds. Best results are ordinarily obtained when the impregnation solution is an aqueous solution of a lanthanide chloride or a lanthanide nitrate. This lanthanide series component can be added to the carrier material, either prior to, simultaneously with, or after the other metallic components are combined therewith. Best results are usually achieved when this component is added simultaneously with the platinum group component. In fact, excellent results have been obtained, as reported in the examples, with a one step impregnation procedure of a tin-containing aluminum carrier material using an aqueous solution comprising the desired amounts of chloroplatinic acid, a lanthanide nitrte, and hydrochloric acid.

It is essential to incorporate a halogen component into the multimetallic catalytic composite of the present invention in an amount sufficient to incorporate an acidic function therein. although the precise form of the chemistry of the association of the halogen component with the carrier material is not entirely known, it is customary in the art to refer to the halogen component as being combined with the carrier material, or with the other ingredients of the catalyst in the form of the halide (e.g. as the chloride). This combined halogen may be either fluorine, chlorine, bromine, or mixtures thereof. Of these fluorine and, particularly, chlorine are preferred for the purpose of the present invention. The halogen may be added to the carrier material in any suitable maner, either during preparation of the support or before or after the addition of the other components. For example, the halogen may be added, at any stage of the preparation of the carrier material or to the calcined carrier material, as an aqueous solution of a suitable, decomposable halogen-containing compound such as hydrogen fluoride, hydrogen chloride, hydrogen bromide, ammonium chloride, etc. The halogen component or a portion thereof, may be combined with the carrier material during the impregnation of the latter with the metallic components; for example, through the utilization of a mixture of chloroplatinic acid and hydrogen chloride. In another situation, the alumina hydrosol which is typically utilized to form the preferred alumina carrier material may contain halogen and thus contribute at least a portion of the halogen component to the final composite. For reforming, the halogen will be typically combined with the carrier material in an amount sufficient to result in a final composite that contains about 0.1 to about 3.5%, and preferably about 0.5 to about 1.5% by weight of halogen calculated on an elemental basis. In isomerization or hydrocracking embodiments, it is generally preferred to utilize relatively larger amounts of halogen in the catalyst — typically, ranging up to about 10 wt. % halogen calculated on an elemental basis, and more preferably about 1 to about 5 wt. %.

Regarding the preferred amounts of the various metallic components of the subject catalyst, I have found it to be an essential practice to specify the amounts of the lanthanide series component as a function of the amount of the platinum group component. On this basis, the amount of the lanthanide series component is selected so that the atomic ratio of lanthanide series element to the platinum group metal contained in the composite is about 0.1:1 to 1.25:1, with best results obtained when the range is about 0.4:1 to about 1:1. Similarly, it is a preferred practice to select the amount of the tin or lead component to produce a composite containing an atomic ratio of tin or lead to platinum group metal within the broad range of about 0.05:1 to 10:1 However, for this last parameter, the best practice is to select this ratio as follows: (1) for tin, it is about 0.1:1 to 3:1, with the most preferred range being about 0.5:1 to 1.5:1; and, (2) for lead, it is about 0.05:1 to 0.9:1, with the most preferred range being about 0.1:1 to 0.75:1.

Another significant parameter for the present catalyst is the "total metals content" which is defined to be the sum of the platinum group component, the lanthanide series component, and the tin or lead component, calculated on an elemental basis. Good results are ordinarily obtained with the subject catalyst when this parameter is fixed at a value of about 0.15 to about 2.5 wt. %, with best results ordinarily achieved at a metals loading of about 0.3 to about 2 wt. %.

In embodiments of the present invention wherein the instant multimetallic catalytic composite is used for dehydrogenation of dehydrogenatable hydrocarbons or for the hydrogenation of hydrogenatable hydrocarbons, it is ordinarily a preferred practice to include an alkali or alkaline earth metal component in the composite and to maintain the halogen component at the lowest possible value. More precisely, this optional component is selected from the group consisting of the compounds of the alkali metals — cesium, rubidium, potassium, sodium and lithium — and the compounds of the alkaline earth metals — calcium, strontium, barium and magnesium. Generally, good results are obtained in these embodiments when this component constitutes about 0.1 to about 5 wt. % of the composite, calculated on an elemental basis. This optional alkali or alkaline earth metal component can be incorporated in the composite in any of the known ways, with impregnation with an aqueous solution of a suitable water-soluble, decomposable compound being preferred.

An optional ingredient for the multimetallic catalyst of the present invention is a Friedel-Crafts metal halide component. This ingredient is particularly useful in hydrocarbon conversion embodiments of the present invention wherein it is preferred that the catalyst utilized has a strong acid or cracking function associated therewith — for example, an embodiment wherein hydrocarbons are to be hydrocracked or isomerized with the catalyst of the present invention. Suitable metal halides of the Friedel-Crafts type include aluminum chloride, aluminum bromide, ferric chloride, ferric bromide, zinc chloride, and the like compounds, with the aluminum halides and particularly aluminum chloride ordinarily yielding best results. Generally, this optional ingredient can be incorporated into the composite of the present invention by any of the conventional methods for adding metallic halides of this type; however, best results are ordinarily obtained when the metallic halide is sublimed onto the surface of the carrier material according to the preferred method disclosed in U.S. Pat. No. 2,999,074. The component can generally be utilized in any amount which is catalytically effective, with a value selected from the range of about 1 to about 100 wt. % of the carrier material generally being preferred.

Regardless of the details of how the components of the catalyst are combined with the porous carrier material, the final catalyst generally will be dried at a temperature of about 200 to about 600° F. for a period of at least about 2 to 24 hours or more, and finally calcined or oxidized at a temperature of about 700° F. to about 1100° F. in an air atmosphere for a period of about 0.5 to about 10 hours in order to convert substantially all of the metallic components to the corresponding oxide forms. Because a halogen component is utilized in the catalyst, best results are generally obtained when the halogen content of the catalyst is adjusted during the calcination step by including a halogen or a halogen-containing compound in the air atmosphere utilized. In particular, when the halogen component of the catalyst is combined chloride, it is preferred to use a mole ratio of $H_2O$ to HCl of about 5:1 to about 100:1 during at least a portion of the calcination step in order to adjust the final chlorine content of the catalyst to a range of about 0.1 to about 3.5 wt. %.

It is an essential feature of the present invention that the resultant oxidized trimetallic catalytic composite is subjected to a substantially water-free reduction step prior to its use in the conversion of hydrocarbons. This step is designed to insure a uniform and finely divided dispersion of the metallic components throughout the carrier material and to selectively reduce the platinum group component to the corresponding metal while maintaining substantially all of the tin or lead component and the lanthanide series component in positive oxidation states. Preferably, substantially pure and dry gydrogen (i.e. less than 20 vol. ppm. $H_2O$) is used as the reducing agent in this step. The reducing agent is contacted with the oxidized catalyst at conditions including a temperature of about 800° F. to about 1200° F. and a period of time of about 0.5 to 2 hours effective to reduce sustantially all of the platinum group component to the elemental metallic state while maintaining substantially all of the tin or lead component and the lanthanide series component in oxidation states above that of the corresponding elemental metals. This reduction treatment may be performed in situ as part of a start-up sequence if precautions are taken to predry the plant to a substantially water-free state and if substantially water-free hydrogen is used.

The resulting reduced catalytic composite may, in some cases, be beneficially subjected to a presulfiding operation designed to incorporate in the catalytic composite from about 0.05 to about 0.5 wt. % sulfur calculated on an elemental basis. Preferably, this presulfiding treatment takes place in the presence of hydrogen and a suitable sulfur-containing and metallic sulfide-producing compound such as hydrogen sulfide, lower molecular weight mercaptans, organic sulfides, disulfides, etc. Typically, this procedure comprises treating the selectively reduced catalyst with a sulfiding gas such as a mixture of hydrogen and hydrogen sulfide having about 10 moles of hydrogen per mole of hydrogen sulfide at conditions sufficient to effect the desired incorporation of sulfur, generally including a temperature ranging from about 50° F. up to about 1100° F. or more. It is generally a good practice to perform this presulfiding step under substantially water-free conditions.

According to the present invention, a hydrocarbon charge stock and hydrogen are contacted with the acidic multimetallic catalyst of the present invention in a hydrocarbon conversion zone. This contacting may be accomplished by using the catalyst in a fixed bed system, a moving bed system, a fluidized bed system, or in a batch type operation; however, a view of the danger of attrition losses of the valuable catalyst and of well known operational advantages, it is preferred to use a fixed bed system. In this system, a hydrogen-rich gas and the charge stock are preheated by any suitable heating means to the desired reaction temperature and then are passed, into a conversion zone containing a fixed bed of the catalyst type previously characterized. It is, of course, understood that the conversion zone may be one or more separate reactors with suitable means therebetween to insure that the desired conversion temperature is maintained at the entrance to each reactor. It is also important to note that the reactants may be contacted with the catalyst bed in either upward, downward, or radial flow fashion with the latter being preferred. In addition, the reactants may be in the liquid phase, a mixed liquid-vapor phase, or a vapor phase when they contact the catalyst, with best results obtained in the vapor phase.

In the case where the multimetallic catalyst of the present invention is used in a reforming operation, the reforming system will comprise a reforming zone containing a fixed bed of the catalyst type previously characterized. This reforming zone may be one or more separate reactors with suitable heating means therebetween to compensate for the endothermic nature of the reactions that take place in each catalyst bed. The hydrocarbon feed stream that is charged to this reforming system will comprise hydrocarbon fractions containing naphthenes and paraffins that boil within the gasoline range. The preferred charge stocks are those consisting essentially of naphthenes and paraffins, although in some cases aromatics and/or olefins may also be present. This preferred class includes straight run gasolines, natural gasolines, synthetc gasolines, partially reformed gasolines and the like. On the other hand, it is frequently advantageous to charge thermally or catalytically cracked gasolines or higher boiling fractions thereof. Mixtures of straight run and cracked gasolines can also be used to advantage. The gasoline charge stock may be a full boiling gasoline having an initial boiling point of from about 50° F. to about 150° F. and an end boiling point within the range of from about 325° F. to about 425° F., or may be a selected fraction thereof which generally will be a higher boiling fraction commonly referred to as a heavy naphtha —for example, a naphtha boiling in the range of $C_7$ to 400° F. In some cases, it is also advantageous to charge pure hydrocarbons or mixtures of hydrocarbons that have been extracted from hydrocarbon distillates —for example, straight-chain paraffins —which are to be converted to aromatics. It is preferred that these charge stocks be treated by conventional catalytic pretreatment methods such as hydrorefining, hydrotreating, hydrodesulfurization, etc., to remove substantially all sulfurous, nitrogenous and water-yielding contaminants therefrom and to saturate any olefins that may be contained therein.

In other hydrocarbon conversion embodiments, the charge stock will be of the conventional type customarily used for the particular kind of hydrocarbon conversion being effected. For example, in a typical isomerization embodiment the charge stock can be a paraffinic stock rich in $C_4$ to $C_8$ normal paraffins, or a normal butane-rich stock, or an n-hexane-rich stock, or a mixture of xylene isomers, etc. In a dehydrogenation embodiment, the charge stock can be any of the known dehydrogenatable hydrocarbons such as an aliphatic compound containing 2 to 30 carbon atoms per molecule, a $C_4$ to $C_{30}$ normal paraffin, a $C_8$ to $C_{12}$ alkylaromatic, a naphthene and the like. In hydrocracking embodiments, the charge stock will be typically a gas oil, heavy cracked cycle oil, etc. In addition alkylaromatic and naphthenes can be conveniently isomerized by using the catalyst of the present invention. Likewise, pure hydrocarbons or substantially pure hydrocarbons can be converted to more valuable products by using the trimetallic catalyst of the present invention in any of the hydrocarbon conversion processes, known to the art, that use a dual-function catalyst.

In a reforming embodiment, it is generally preferred to utilize the novel multimetallic catalytic composite in a substantially water-free environment. Essential to the achievement of this condition in the reforming zone is the control of the water level present in the charge stock and the hydrogen stream which is being charged to the zone. Best results are ordinarily obtained when the total amount of water entering the conversion zone from any source is held to a level less than 50 ppm. and preferably less than 20 ppm.; expressed as weight of equivalent water in the charge stock. In general, this can be accomplished by careful control of the water present in the charge stock and in the hydrogen stream. The charge stock can be dried by using any suitable drying means known to the art such as a conventional solid adsorbent having a high selectivity for water; for instance, sodium or calcium crystalline aluminosilicates, silica gel, activated alumina, molecular sieves, anhydrous calcium sulfate, high surface area sodium and the like adsorbents. Similarly, the water content of the charge stock may be adjusted by suitable stripping operations in a fractionation column or like device. And in some cases, a combination of adsorbent drying and distillation drying may be used advantageously to effect almost complete removal of water from the charge stock. Preferably, the charge stock is dried to a level corresponding to less than 20 ppm. of $H_2O$ equivalent. In general, it is preferred to maintain the hydrogen stream entering the hydrocarbon conversion zone at a level of about 10 vol. ppm. of water or less. In the case where the water content of hydrogen stream is above this range, this can be conveniently accomplished by contacting the hydrogen stream with a suitable desiccant such as those mentioned above at conventional drying conditions.

In the reforming embodiment, an effluent stream is withdrawn from the reforming zone and passed through a cooling means to a separation zone, typically maintained at about 25° to 150° F., wherein a hydrogen-rich gas is separated from a high octane liquid product, commonly called an "unstabilized reformate". When a super-dry operation is desired, at least a portion of this hydrogen-rich gas is withdrawn from the separating zone and passed through an absorption zone containing an adsorbent selective for water. The resultant substantially water-free hydrogen stream can then be recycled through suitable compressing means back to the reforming zone. The liquid phase from the separating zone is typically withdrawn and commonly treated in a fractionating system in order to adjust the butane concentration, thereby controlling frontend volatility of the resulting reformate.

The conditions utilized in the numerous hydrocarbon conversion embodiments of the present invention are those customarily used in the art for the particular reaction, or combination of reactions, that is to be effected. For instance, alkylaromatics, olefin, and paraffin isomerization conditions include: a temperature of about 32° F. to about 1000° F. and preferably about 75° F. to about 600° F.; a pressure of atomospheric to about 100 atmospheres; a hydrogen to hydrocarbon mole ratio of about 0.5:1 to about 20:1 and a LHSV (calculated on the basis of equivalent liquid volume of the charge stock contacted with the catalyst per hour divided by the volume of conversion zone containing catalyst) of about 0.2 hr.$^{-1}$ to 10 hr.$^{116\ 1}$. Dehydrogenation conditions include: a temperature of about 700° to about 1250° F., a pressure of about 0.1 to about 10 atmospheres, a liquid hourly space velocity of about 1 to 40 hr.$^{-1}$ and a hydrogen to hydrocarbon mole ratio of about 1:1 to 20:1. Likewise, typically hydrocracking conditions include: a pressure of about 500 psig. to about 3000 psig.; a temperature of about 400° F. to about 900° F.; a LHSV of about 0.1 hr.$^{-1}$ to about 10 hr.$^{-1}$; and hydrogen circulation rates of about 1000 to 10,000 SCF per barrel of charge.

In the reforming embodiment of the present invention the pressure utilized is selected from the range of about 0 psig. to about 1000 psig., with the preferred pressure being about 50 psig. to about 600 psig. Particularly good results are obtained at low pressure; namely, a pressure of about 50 to 350 psig. In fact, it is a singular advantage of the present invention that it allows stable operation at lower pressure than have heretofore been successfully utilized in so-called "continuous" reforming systems (i.e. reforming for periods of about 15 to about 200 or more barrels of charge per pound of catalyst without regeneration) with all platinum monometallic catalysts. In other words, the multimetallic catalyst of the present invention allows the operation of a continuous reforming system to be conducted at low pressure (i.e. 100 to about 350 psig.) for about the same or better catalyst life before regeneration as has been heretofore realized with conventional monometallic catalysts at higher pressures (i.e. 400 to 600 psig.). On the other hand, the stability feature of the present invention enables reforming operation conducted at pressures of 400 to 600 psig. to achieve substantially increased catalyst life before regeneration.

Similarly, the temperature required for reforming is generally lower than that required for a similar reforming operation using a high quality catalyst of the prior art. This significant and desirable feature of the present invention is a consequence of the selectivity of the acidic multimetallic catalyst of the present invention for the octane-upgrading reactions that are preferably induced in a typical reforming operation. Hence, the present invention requires a temperature in the range of from about 800° F. to about 1100° F. and preferably about 900° F. to about 1050° F. As is well known to those skilled in the continuous reforming art, the initial selection of the temperature within this broad range is made primarily as a function of the desired octane of the product reformate considering the characteristics of the charge stock and of the catalyst. Ordinarily, the temperature then is thereafter slowly increased during the run to compensate for the inevitable deactivation that occurs to provide a constant octane product. Therefore, it is a feature of the present invention that the rate at which the temperature is increased in order to maintain a constant octane product, is substantially lower for the catalyst of the present invention than for a high quality reforming catalyst which is manufactured in exactly the same manner as the catalyst of the present invention except for the inclusion of the lanthanide series and tin or lead components. Moreover, for the catalyst of the present invention, the $C_5$ yield loss for a given temperature increase is substantially lower than for a high quality reforming catalyst of the prior art. In addition, hydrogen production is substantially higher.

The reforming embodiment of the present invention also typically utilizes sufficient hydrogen to provide an amount of about 1 to about 20 moles of hydrogen per mole of hydrocarbon entering the reforming zone, with excellent results being obtained when about 5 to about 10 moles of hydrogen are used per mole of hydrocarbon. Likewise, the liquid hourly space velocity (LHSV) used in reforming is selected from the range of about 0.1 to about 10 hr.$^{-1}$, with a value in the range of about 1 to about 5 hr.$^{-1}$ being preferred. In fact, it is a feature of the present invention that it allows operations to be conducted at higher LHSV than normally can be stably achieved in a continuous reforming process with a high quality reforming catalyst of the prior art. This last feature is of immense economic significance because it allows a continuous reforming process to operate at the same throughput level with less catalyst inventory than that heretofore used with conventional reforming catalysts at no sacrifice in catalyst life before regeneration.

The following examples are given to illustrate further the preparation of the acidic multimetallic catalytic composite of the present invention and the use thereof in the conversion of hydrocarbons. It is understood that the examples are intended to be illustrative rather than restrictive.

EXAMPLE I

A tin-containing alumina carrier material comprising 1/16 inch spheres was prepared by: forming an aluminum hydroxyl chloride sol by dissolving substantially pure aluminum pellets in a hydrochloric acid solution, adding stannic chloride to the resulting sol in an amount selected to result in a finished catalyst containing about 0.5 wt. % tin, adding hexamethylenetetramine to the resulting tin-containing alumina sol, gelling the resulting solution by dropping it into an oil bath to form spherical particles of an aluminum- and tin-containing hydrogel, aging and washing the resulting particles and finally drying and calcining the aged and washed particles to form spherical particles of gamma-alumina containing a uniform dispersion of about 0.5 wt. % tin in the form of tin oxide and about 0.3 wt. % combined chloride. Additional details as to this method of preparing the preferred gamma-alumina carrier material are given in the teachings of U.S. Pat. No. 2,620,314.

An aqueous impregnation solution containing chloroplatinic acid, neodymium nitrate and hydrogen chloride was then prepared. The tin-containing alumina carrier material was thereafter admixed with the impregnation solution. The amount of reagents contained in this impregnation solution was calculated to result in a final composite containing, on an elemental basis, 0.47 wt. % platinum, 0.26 wt. % neodymium and 0.5 wt. % tin. In order to insure uniform dispersion of the metallic components throughout the carrier material, the amount of hydrochloric acid used was about 3 wt. % of the alumina particles. This impregnation step was performed by adding the carrier material particles to the impregnation mixture with constant agitation. In addition, the volume of the solution was approximately the same as the volume of the carrier material particles. The impregnation mixture was maintained in contact with the carrier material particles for a period of about ½ hour at a temperature of about 70° F. Thereafter, the temperature of the impregnation mixture was raised to about 225° F. and the excess solution was evaporated in a period of about 1 hour. The resulting dried particles were then subjected to a calcination or oxidation treatment in an air atmosphere at a temperature of about 975° F. for about 1 hour. This oxidation step was designed to convert substantially all of the metallic ingredients to the corresponding oxide forms. The calcined spheres were then contacted with an air stream containing $H_2O$ and HCl in a mole ratio of about 30:1 for about 4 hours at 975° F. in order to adjust the halogen content of the catalyst particles to a value of about 1.05 wt. %.

The resulting catalyst particles were analyzed and found to contain, on an elemental basis, about 0.47 wt. % platinum, about 0.26 wt. % neodymium, about 0.5 wt. % tin and about 1.05 wt. % chloride. For this catalyst, the atomic ratio of tin to platinum is 1.75:1 and the atomic ratio of neodymium to platinum is 0.75:1.

Thereafter, the catalyst particles were subjected to a dry pre-reduction treatment, designed to reduce the platinum component to the elemental state while maintaining the tin and neodymium components in positive oxidation states, by contacting them for 1 hour with a substantially pure hydrogen stream containing less than 5 vol. ppm. $H_2O$ at a temperature of about 1050° F., a pressure slightly above atmospheric, and a flow rate of the hydrogen stream through the catalyst particles corresponding to a gas hourly space velocity of about 720 hr.$^{-1}$. The resulting catalyst is hereinafter referred to as catalyst "A".

EXAMPLE II

In order to compare the novel acidic multimetallic catalytic composite of the present invention with a leading bimetallic catalytic composite of the prior art in a manner calculated to bring out the beneficial interaction between the lanthanide series component and a platinum- and tin-containing catalyst, a comparison test was made between the catalyst of the present invention, which was prepared in Example I (i.e. catalyst A), and a superior bimetallic reforming catalyst of the prior art which contained a combination of platinum and tin as its hydrogenation-dehydrogenation component. The control catalyst was a combination of a platinum component, a tin component and a chloride component with a gamma-alumina carrier material in an amount sufficient to result in the final catalyst containing about 0.6 wt. % platinum, about 0.5 wt. % tin and about 1.05 wt. % chloride. The control catalyst is hereinafter referred to as catalyst "B". Catalyst B was prepared by a method identical to that set forth in Example I except for the inclusion of the lanthanide series element and the increase in the platinum component from 0.47 wt. % to 0.6 wt. %.

These catalysts were then separately subjected to a high stress accelerated catalytic reforming evaluation test designed to determine in a relatively short period of time their relative activity, selectivity and stability characteristics in a process for reforming a relatively low-octane gasoline fraction. In both tests the same charge stock was utilized and its pertinent characteristics are set forth in Table I. It is to be noted that in both cases the test was conducted under substantially water-free conditions with the only significant source of water being the 5 wt. ppm. present in the charge stock. Likewise, it is to be observed that both runs were performed under substantially sulfur-free conditions with the only sulfur input into the plant being the 0.1 wt. % sulfur contained in the charge stock.

TABLE I

| Analysis of Charge Stock | |
|---|---|
| Gravity, API at 60° F. | 60.3 |
| Distillation Profile, ° F. | |
| Initial Boiling Point | 162 |
| 5% Boiling Point | 186 |
| 10% Boiling Point | 200 |
| 30% Boiling Point | 224 |
| 50% Boiling Point | 252 |
| 70% Boiling Point | 286 |
| 90% Boiling Point | 322 |
| 95% Boiling Point | 338 |
| End Boiling Point | 364 |
| Chloride, wt. ppm. | 0.1 |
| Nitrogen, wt. ppm. | 0.1 |
| Sulfur, wt. ppm. | 0.1 |
| Water, wt. ppm. | 5 |
| Octane Number, F-1 Clear | 43.8 |
| Paraffins, vol. % | 67.1 |
| Naphthenes, vol. % | 21.8 |
| Aromatics, vol. % | 11.1 |

This accelerated reforming test was specifically designed to determine in a very short period of time whether the catalyst being evaluated has superior characteristics for use in a high severity reforming operation. Each run consisted of a series of evaluation periods of 24 hours each, each of these periods comprised a 12 hour line-out period followed by a 12 hour test period during which the $C_5$+ product reformate from the plant was collected and analyzed. Both test runs were performed at identical conditions which comprised a liquid hourly space velocity (LHSV) of 2.0 hr.$^{-1}$, a pressure of 100 psig., a 5:1 gas to oil ratio, and an inlet reactor temperature which was continuously adjusted throughout the test in order to achieve and maintain a $C_5$+ target octane of 102 F-1 clear.

Both tests were performed in a pilot plant scale reforming unit comprising a reactor containing the catalyst undergoing evaluation, a hydrogen separation zone, a debutanizer column and suitable heating means, pumping means, condensing means, compressing means and the like conventional equipment. The flow scheme utilized in this plant includes commingling a hydrogen recycle stream with the charge stock and heating the resulting mixture to the desired conversion temperature. The heated mixture is then passed downflow into a reactor containing the catalyst undergoing evaluation as a stationary bed. An effluent stream is then withdrawn from the bottom of the reactor, cooled to about 70° F. and passed to a gas-liquid separation zone wherein a hydrogen-rich gaseous phase separates from a liquid hydrocarbon phase. A portion of the gaseous phase is then continuously passed through a high surface area sodium scrubber and the resulting substantially water-free and sulfur-free hydrogen stream is returned to the reactor in order to supply the hydrogen recycle stream. The excess gaseous phase from the separation zone is recovered as the hydrogen-containing product stream (commonly called "excess recycle gas"). The liquid phase from the separation zone is withdrawn therefrom and passed to a debutanizer column wherein lightends (i.e. $C_1$ to $C_4$) are taken overhead as debutanizer gas and a $C_5$+ reformate stream recovered as the principal bottom product.

The results of the separate test performed on the particularly preferred catalyst of the present invention, Catalyst A, and the control catalyst, Catalyst B, are presented for each test period in Table II in terms of inlet temperature to the reactor in ° F. necessary to achieve the target octane level, the amount of $C_5$+ reformate recovered expressed as vol. % of the charge stock, and the purity of the recycle gas expressed as mole % hydrogen contained in same. These results are shown in Table II as a function of time expressed in barrels of charge processed per pound of catalyst in the reactor (BPP).

TABLE II

| | Results of Accelerated Reforming Test | | | | | |
|---|---|---|---|---|---|---|
| | CATALYST "A" | | | CATALYST "B" | | |
| T, BPP | T, ° F | $C_5$+, wt. % | $H_2$, % | T, ° F | $C_5$+, wt.% | $H_2$,% |
| 0.4 | 968 | 77.4 | 86.0 | 967 | 77.0 | 86.4 |
| 0.6 | 971 | 77.8 | 86.7 | 975 | 77.0 | 86.7 |
| 0.8 | 978 | — | 86.3 | 983 | 77.1 | 87.0 |
| 1.0 | 984 | 77.0 | 85.8 | 992 | 76.6 | 86.2 |
| 1.2 | 988 | 77.2 | 86.5 | 999 | 76.5 | 85.6 |
| 1.5 | 1004 | — | 85.0 | 1013 | 76.0 | 84.0 |
| 1.7 | 1010 | — | 84.3 | — | — | — |

Referring now to the results of the comparison test presented in Table II, it is evident that the effect of the lanthanide series component on the platinum and tin bimetallic catalyst is to substantially promote same and to enable a catalyst containing less platinum to outperform a catalyst containing a substantially greater amount of platinum in the areas of activity, selectivity and stability. That is, the data presented in Table II clearly indicates that the catalyst of the present invention is markedly superior to the control catalyst in a high severity reforming process. As was pointed out in detail hereinbefore, a good measure of activity for a reforming catalyst is the inlet temperature in the reactor which is required to make target octane and the data presented in Table II on this variable clearly shows that catalyst A was significantly more active than catalyst B; for example, at a time corresponding to 1.5 barrels of charge per pound of catalyst, catalyst A required a reactor inlet temperature of 1004° F. in order to make octane which stands in sharp contrast to the 1013° F. requirement of catalyst B at the same point in the run. This 9° F. difference in temperature requirement for octane is conclusive evidence of the ability of the catalyst of the present invention to materially accelerate the rate of the involved reforming reaction in view of the well known rule of thumb that the rate of reaction doubles with every 10° C. change in reactor temperature. Thus the data clearly shows that the composite of the present invention was materially more active than the control catalyst. However, activity is only one of the necessary characteristics needed in order for a catalyst to demonstrate superiority. Activity characteristics must be coupled with superior selectivity and stability characteristics in order to demonstrate improved performance. Selectivity is measured directly by $C_5+$ yield and the data presented in Table II clearly indicates that catalyst A consistently produced better yields than catalyst B. (It is to be noted that the dashes in Table II represent periods where the relevant analyses of the product streams were not made.) Another indication of good selectivity characteristics is the hydrogen content of the excess recycle gas and on this basis the catalyst of the present invention exhibited hydrogen purity which was analogous to that observed for catalyst B. On the other hand, good stability characteristics are shown by the rate of change of the activity and selectivity parameters as was explained hereinbefore, and on the basis the incremental change in temperature required to maintain octane and in $C_5+$ yield exhibited in Table II clearly shows superior stability for the catalyst of the present invention.

In summary, it is clear from the data presented in Table II that a lanthanide series element, neodymium, is an efficient and effective promoter for a platinum- and tin-containing reforming catalyst in a high severity reforming operation.

It is intended to cover by the following claims, all changes and modifications of the above disclosure of the present invention which would be self-evident to a man of ordinary skill in the hydrocarbon conversion art or the catalyst formulation art.

I claim as my invention:

1. A process for converting a hydrocarbon which comprises contacting the hydrocarbon at hydrocarbon conversion conditions with an acidic catalytic composite comprising a porous carrier material containing, on an elemental basis, about 0.01 to about 2 wt. % platinum group metal, about 0.01 to about 5 wt. % tin or lead, about 0.1 to about 3.5 wt. % halogen, and a lanthanide series component in an amount sufficient to result in an atomic ratio of lanthanide series component to platinum group metal of about 0.1:1 to about 1.25:1, wherein the platinum group metal, tin or lead, and lanthanide series component are uniformly dispersed throughout the porous carrier material, wherein substantially all of the platinum group metal is present in the elemental metallic state, wherein substantially all of the tin or lead is present in an oxidation state above that of the corresponding elemental metal, and wherein substantially all of the lanthanide series component is present in an oxidation state above that of the corresponding elemental metal.

2. A process as defined in claim 1 wherein the platinum group metal is platinum.

3. A process as defined in claim 1 wherein the platinum group metal is palladium.

4. A process as defined in claim 1 wherein the platinum group metal is iridium.

5. A process as defined in claim 1 wherein the halogen component is combined chloride.

6. A process as defined in claim 1 wherein the porous carrier material is a refractory inorganic oxide.

7. A process as defined in claim 6 wherein the refractory inorganic oxide is alumina.

8. A process as defined in claim 1 wherein the lanthanide series component is neodymium.

9. A process as defined in claim 1 wherein the lanthanide series component is cerium.

10. A process as defined in claim 1 wherein the lanthanide series component is lanthanum.

11. A process as defined in claim 1 wherein the lanthanide series component is present in the catalytic composite in an amount sufficient to result in an atomic ratio of lanthanide series component to platinum group metal of about 0.4:1 to about 1:1.

12. A process as defined in claim 1 wherein substantially all of the tin or lead is present in the catalytic composite as the corresponding oxide.

13. A process as defined in claim 1 wherein substantially all of the lanthanide series component is present in the catalytic composite in the form of the corresponding oxide.

14. A process as defined in claim 1 wherein the atomic ratio of tin or lead to platinum group metal contained in the composite is about 0.05:1 to about 10:1.

15. A process as defined in claim 1 wherein the catalytic composite contains about 0.05 to about 1 wt.% platinum group metal, about 0.05 to about 2 wt.% tin or lead, 0.5 to about 1.5 wt.% halogen, and an atomic ratio of lanthanide series component to platinum group metal of about 0.4:1 to about 1:1.

16. A process as defined in claim 1 wherein the contacting of the hydrocarbon with the catalytic composite is performed in the presence of hydrogen.

17. A process as defined in claim 1 wherein the type of hydrocarbon conversion is catalytic reforming of a gasoline fraction to produce a high-octane reformate, wherein the hydrocarbon is contained in the gasoline fraction, wherein the contacting is performed in the presence of hydrogen and wherein the hydrocarbon conversion conditions are reforming conditions.

18. A process as defined in claim 17 wherein the reforming conditions include a temperature of about 800° to 1100° F., a pressure of about 0 to about 1000 psig., a liquid hourly space velocity of about 0.1 to about 10 hr.$^{-1}$, and a mole ratio of hydrogen to hydrocarbon of about 1:1 to about 20:1.

19. A process as defined in claim 17 wherein the contacting step is performed in a substantially water-free environment.

20. A process as defined in claim 17 wherein the reforming conditions include a pressure of about 50 to about 350 psig.

* * * * *